United States Patent [19]

Agrawal et al.

[11] Patent Number: 5,605,890
[45] Date of Patent: Feb. 25, 1997

[54] CYCLODEXTRIN CELLULAR DELIVERY SYSTEM FOR OLIGONUCLEOTIDES

[75] Inventors: Sudhir Agrawal, Shrewsbury; Qiuyan Zhao, Worcester; Ivan Habus, Shrewsbury, all of Mass.

[73] Assignee: Hybridon, Inc., Worcester, Mass.

[21] Appl. No.: 480,833

[22] Filed: Jun. 7, 1995

Related U.S. Application Data

[60] Division of Ser. No. 341,522, Nov. 17, 1994, which is a continuation-in-part of Ser. No. 252,072, Jun. 1, 1994, abandoned.

[51] Int. Cl.$^6$ .............................. A61K 48/00; C12N 7/06
[52] U.S. Cl. .............................. 514/44; 514/58; 435/238; 536/24.5; 935/34; 935/52
[58] Field of Search ................ 514/44, 58; 536/103, 536/23.1, 24.5; 435/238, 240.2; 424/488

[56] References Cited

U.S. PATENT DOCUMENTS

| | | | |
|---|---|---|---|
| 4,806,463 | 2/1989 | Goodchild et al. | 435/5 |
| 5,457,187 | 10/1995 | Gmeiner et al. | 536/25.5 |

FOREIGN PATENT DOCUMENTS

| | | |
|---|---|---|
| 5170650 | 9/1993 | Japan. |
| WO90/00596 | 1/1990 | WIPO. |
| WO91/02040 | 2/1991 | WIPO. |
| WO93/23570 | 11/1993 | WIPO. |
| WO94/01448 | 1/1994 | WIPO. |

OTHER PUBLICATIONS

R Weiss (1991) Science News 139:108–109.
CA Stein et al (1993) Science 261:1004–1012.
RI Gelb et al (1983) Life Sciences 33:83–85.
T Loftsson et al (1991) PZ Wissenschaft 136:5–10.
N Miller et al (1994) Parasitology Today 10:92–97.
RA Stull et al (1995) Pharmaceutical Research 12:465–483.
S Wu-Pong (1994) Pharmaceutical Technology 118:102–114.
RW Wagner (1994) Nature 372:333–335.
JL Hoffman et al (1970) Biochemistry 9:3542–3550.
Horiuchi et al. (1990) *J. Pharmaceut. Sci.* 79:128–132.
Jansen et al. (1990) *Lens Eye Tox. Res.* 7:459–468.
Misiura et al. (1990) *J. Nucleic Acids Res.* 18:4345–4353.
Yoshida et al. (1990) *Chem. Pharm. Bull.* 38:176–179.
Brewster et al. (1991) *Pharmaceut. Res.* 8:792–795.
Merkus et al. (1991) *Pharmaceut. Res.* 8:588–592.
Moriya et al. (1991) *J. Med. Chem.* 34:2301–2304.
Muller et al. (1991) *J. Pharmaceut. Sci.* 80:599–604.
Pardridge et al. (1991) *FEBS Lett.* 288:30–32.
Pitha et al. (1991) *J. Pharmaceutic Res.* 8:1151–1154.
Simpkins et al. (1991) *J. Parenteral Sci. Technol.* 45:266–269.
Yaksh et al. (1991) *Life Sci.* 48:623–633.
Arima et al. (1992) *J. Pharm. Soc. Japan* 112:65–72 (Abstract only).
Bennett et al. (1992) *Mol. Pharmacol.* 41:1023–1033.
Nakanishi et al. (1992) *Chem. Pharm. Bull.* 40:1252–1256.
Shao et al. (1992) *Pharm. Res.* 9:1157–1163.
Weiner et al. (1992) *Pathobiol.* 60:206–212.
Barry et al. (1993) *Biotechniques* 15:1016–1018.
Brinker et al. (1993) *Angew. Chem. Int. Ed. Engl.* 32:1344–1345.
Krieg et al. (1993) *Proc. Natl. Acad. Sci. (USA)* 90:1048.

(List continued on next page.)

*Primary Examiner*—Bruce R. Campbell
*Attorney, Agent, or Firm*—Hale and Dorr

[57] ABSTRACT

Disclosed is a composition including an oligonucleotide complexed with a cyclodextrin. The oligonucleotide may be noncovalently associated with the cyclodextrin. Alternatively, the oligonucleotide may be covalently complexed with adamantane which is noncovalently associated with the cyclodextrin. Also disclosed are methods of enhancing the cellular uptake and intracellular concentration of oligonucleotides, methods of increasing the solubility of an oligonucleotide in a cell, and methods of treating a cell for viral infection or to prevent viral infection.

2 Claims, 9 Drawing Sheets

OTHER PUBLICATIONS

Uekama et al. (1993) *J. Pharm. Pharmacol.* 45:745–747.
Ueno et al. (1993) *J. Am. Chem. Soc.* 115:12575–12576.
Weisz et al. (1993) *Biochem. Pharmacol.* 45:1011–1016.
Zelphati et al. (1993) *Antisense Res. Dev.* 3:323–338.
Zhao et al. (1993) *Antisense Res. Dev.* 3:53–56.
Gerloczy et al. (1994) *J. Pharmaceut. Sci.* 83:193–196.
Zamecnick (1994) *Proc. Natl. Acad. Sci. (USA)* 91:3156.
Irie, Tetsumi et al., (1992), *J. Pharmaceut. Sciences*, 81(6), 524–528.
Brewster, Marcus E., et al., (1991), *Journal of Pharmaceutical Sciences*, 80(4), 380–383.
Frijlink, Henderik W., et al, (1991), *Pharmaceutical Research*, 8(3), 380–384.
Huraux et al., (1989), *Rev. Pneumol. Clin.*, 45, 99–105.
Agrawal et al., (1992), *Antisense Res. & Dev.*, 2, 261–266.
Loke et al. (1989) *Proc. Natl. Acad. Sci. (USA)* 86:3474.
Yakubov et al. (1989) *Proc. Natl. Acad. Sci. (USA)* 86:6454.
Anand et al. (1990) *Antiviral Chem. Chemother.* 1:41–46.

FIG. 1A
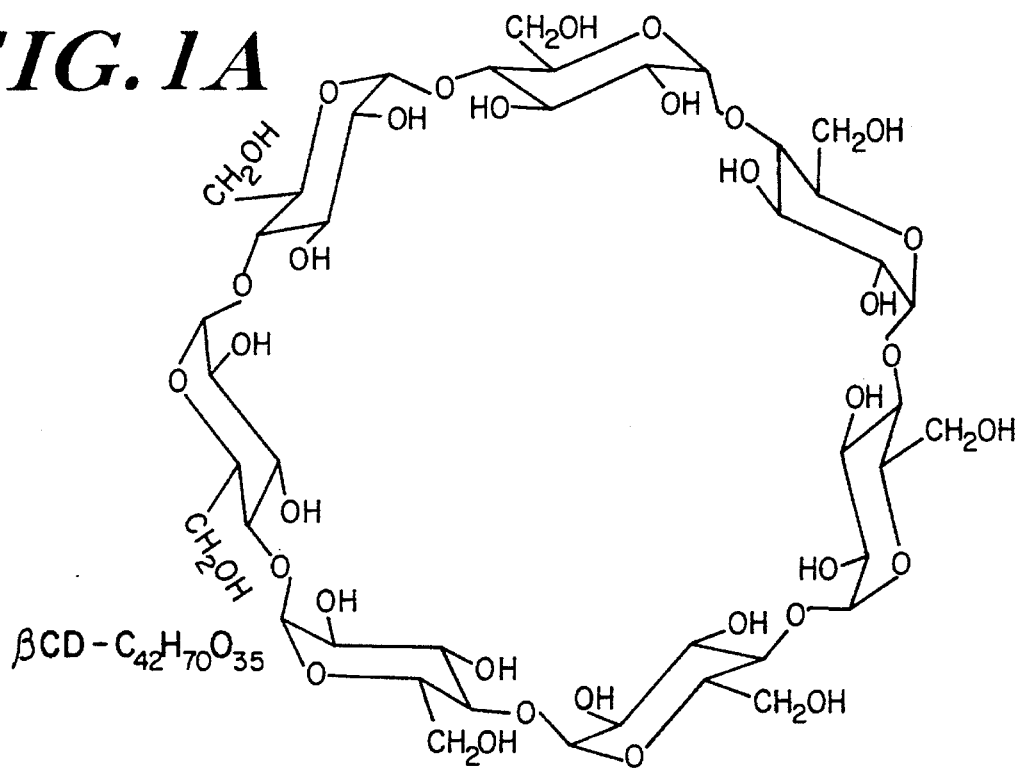
βCD-C$_{42}$H$_{70}$O$_{35}$
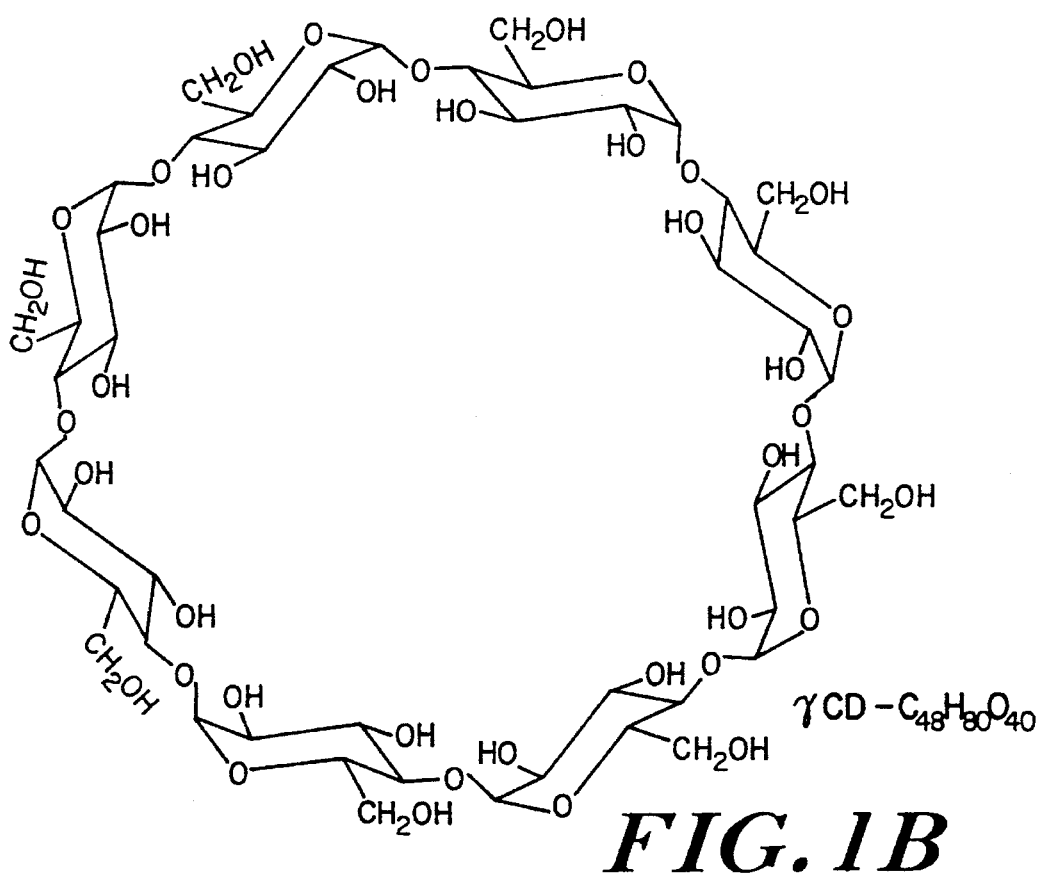
γCD-C$_{48}$H$_{80}$O$_{40}$
FIG. 1B

SEQ ID NO:7 PO

SEQ ID NO:8 PS

SEQ ID NO:9 PS

SEQUENCE LISTING ( 1 ) GENERAL INFORMATION:

( i i i ) NUMBER OF SEQUENCES: 2

( 2 ) INFORMATION FOR SEQ ID NO:1:

(  i  ) SEQUENCE CHARACTERISTICS:
    ( A ) LENGTH: 25
    ( B ) TYPE: nucleic acid
    ( C ) STRANDEDNESS: single
    ( D ) TOPOLOGY: linear (  i  i  ) MOLECULE TYPE:

(  i  i  i  ) HYPOTHETICAL: NO (  i  v  ) ANTI-SENSE: YES (  x  i  ) SEQUENCE DESCRIPTION: SEQ ID NO:1:

CTCTCGCACC CATCTCTCTC CTTCT 25

( 2 ) INFORMATION FOR SEQ ID NO:2:

(  i  ) SEQUENCE CHARACTERISTICS:
    ( A ) LENGTH: 6
    ( B ) TYPE: nucleic acid
    ( C ) STRANDEDNESS: single
    ( D ) TOPOLOGY: linear (  i  i  ) MOLECULE TYPE: cDNA (  i  i  i  ) HYPOTHETICAL: NO (  i  v  ) ANTI-SENSE: YES (  x  i  ) SEQUENCE DESCRIPTION: SEQ ID NO:2:

CCGACG 6

CYCLODEXTRIN CELLULAR DELIVERY SYSTEM FOR OLIGONUCLEOTIDES

CROSS-REFERENCE TO RELATED APPLICATION

This is a divisional application of patent application Ser. No. 08/341,522, entitled "CYCLODEXTRIN CELLULAR DELIVERY SYSTEM FOR OLIGONUCLEOTIDES", filed on Nov. 17, 1994, and assigned to the present assignees, which is a continuation-in-part of patent application Ser. No. 08/252,072 entitled "CYCLODEXTRIN CELLULAR DELIVERY SYSTEM FOR OLIGONUCLEOTIDES", filed Jun. 1, 1994, now abandoned, and is related to patent application Ser. No. 08/480,834, entitled "CYCLODEXTRIN CELLULAR DELIVERY SYSTEM FOR OLIGONUCLEOTIDES", filed on Jun. 7, 1995, assigned to the present assignees.

BACKGROUND OF THE INVENTION

This invention relates to antisense therapy. More particularly, this invention relates to compositions and methods for enhancing the cellular uptake of antisense oligonucleotides.

New chemotherapeutic agents have been developed which are capable of modulating cellular and foreign gene expression. These agents, called antisense oligonucleotides, are single-stranded oligonucleotides which bind to a target nucleic acid molecules according to the Watson-Crick or Hoogsteen rule of base pairing, and in doing so, disrupt the function of the target by one of several mechanisms: by preventing the binding of factors required for normal transcription, splicing, or translation; by triggering the enzymatic destruction of RNA by RNase H, or by destroying the target via reactive groups attached directly to the antisense oligonucleotide. Thus, they have become widely used research tools for inhibiting gene expression sequence specifically, and are under investigation for possible use as therapeutic agents (see, e.g., Agrawal et al. (*Proc. Natl. Acad. Sci. (USA)* (1993) 90:3860–3884); Bayever et al. (1992) *Antisense Res. Development* 2: 109–110).

In order for antisense molecules to have therapeutic value, they must have the ability to enter a cell and contact target endogenous nucleic acids. Furthermore, they must be able to withstand the rigors of the highly nucleolytic environment of the cell.

Recent studies have shown that certain modifications to oligonucleotides, such as artificial internucleotide linkages, not only render the oligonucleotides resistant to nucleolytic degradation (see, e.g., Agrawal et al. (1988) *Proc. Natl. Acad. Sci. (USA)* 85: 7079–7083; Agrawal et al. (1989) *Proc. Natl. Acad. Sci. (USA)* 86: 7790–7794; Gao et al. (1990) *Antimicrob. Agents Chem.* 34:808; and Storey et al. (1991) *Nucleic Acid Res.* 19:4109), but also may increase cellular uptake of the oligonucleotide. For example, oligonucleotides with phosphorothioate or methylphosphonate internucleotide linkages have been found to bind to, and to be taken up by cells more readily than phosphodiester-linked oligonucleotides (Zhao et al. (1993) *Antisense Res. Dev.* 3:53–56).

Oligonucleotide uptake is saturable, sequence-independent, and temperature and energy dependent. While there is some evidence to suggest that such uptake may occur through a 80,000 dalton membrane protein (Loke et al. (1989) *Proc. Natl. Acad. Sci. (USA)* 86:3474; Yakubov et al. (1989) *Proc. Natl. Acad. Sci. (USA)* 86:6454), the gene for this protein has not yet been cloned or characterized. One study suggests internalization of the oligonucleotide is by a caveolar, potocytotic mechanism rather than by endocytosis (Zamecnick (1994) *Proc. Natl. Acad. Sci. (USA)* 91:3156). Whether oligonucleotides are internalized via a receptor-mediated endocytotic pathway, a pinocytic mechanism, or a combination of both remains poorly understood.

To improve on the cellular uptake of oligonucleotides, the oligonucleotides have been modified in ways other than those described above. For example, WO 9323570 discloses an oligonucleotide with improved cellular uptake having at least one nucleotide residue covalently linked at its 2' position with various molecules including an amino acid, polypeptide, protein, sugar, sugar phosphate, neurotransmitter, hormone, cyclodextrin, starch, steroid, or vitamin. Enhanced cellular uptake of biotinylated oligonucleotide in the presence of avidin has also been demonstrated (Partridge et al. (1991) *FEBS Lett.* 288:30–32).

In addition, phosphodiester-linked oligodeoxynucleotides have been introduced into cells by the pore-forming agent streptolysin O (Barry et al. (1993) *Biotechniques* 15:1016–1018), and a liposomal preparation including cationic lipid has been shown to enhance the cellular uptake of antisense molecules targeted to a portion of the human intercellular adhesion molecule (Bennett et al. (1992) *Mol. Pharmacol.* 41:1023–1033). phosphodiester-linked oligonucleotides bearing a 5'-cholesteryl modification show increased cellular uptake and biological effects (Krieg et al. (1993) *Proc. Natl. Acad. Sci. (USA)* 90:1048). Antibody-targeted liposomes have also been used to enhance the cellular uptake of oligonucleotides targeted to HLA class I molecules expressed by HIV-infected cells (Zelphati et al. (1993) *Antisense Res. Dev.* 3:323–338).

However, improved uptake Of modified and unmodified oligonucleotides both in vitro and in vivo is obviously desirable. There is therefore a need for improved compositions and methods for enhancing the cellular uptake of antisense oligonucleotides. Such enhancement would ultimately result in an increased efficacy of antisense oligonucleotides and a reduction in the dose administered. Ideally, such compositions and methods will also be useful for increasing the general solubility of oligonucleotides.

SUMMARY OF THE INVENTION

It has been discovered that the uptake of antisense oligonucleotides into cells can be enhanced by noncovalently associating such oligonucleotides with a cyclodextrin. This discovery has been exploited to produce the various compositions and methods for enhancing the cellular uptake of antisense oligonucleotides.

In one aspect of the invention, a composition including an oligonucleotide noncovalently associated with a cyclodextrin is provided. In one preferred embodiment, the oligonucleotide is noncovalently associated directly to a beta (β)-cyclodextrin, a gamma (γ)-2-cyclodextrin, a methyl substituted cyclodextrin, or a derivative thereof. Preferred derivatives include 2-hydroxypropyl-β-cyclodextrin, hydroxypropyl-γ-cyclodextrin, hydroxyethyl-β-cyclodextrin, β-cyclodextrin polysulfate, trimethyl β-cyclodextrin, γ-cyclodextrin polysulfate, and methyl substituted cyclodextrins.

In some embodiments of the invention, the oligonucleotide to which the cyclodextrin is complexed contains at least one deoxyribonucleotide, one ribonucleotide, or both deoxyribonucleotides and ribonucleotides (i.e., a hybrid oligonucleotide). The oligonucleotide is interconnected with phosphodiester internucleotide linkages in some embodiments, while in others, the oligonucleotide is modified.

The term "modified oligonucleotide" is used herein as an oligonucleotide in which at least two of its nucleotides are covalently linked via a synthetic linkage, i.e., a linkage other than a phosphodiester between the 5' end of one nucleotide and the 3' end of another nucleotide in which the 5' nucleotide phosphate has been replaced with any number of chemical groups. Preferable synthetic linkages include alkylphosphonates, phosphate esters, alkylphosphonates, phosphorothioates, phosphorodithioates, 2-O-methyl carbonates, alkylphosphonothioates, phosphoramidates, carbamates, phosphate triesters, acetamidate, and carboxymethyl esters. In one preferred embodiment of the invention, the oligonucleotide comprises at least one phosphorothioate and/or one alkylphosphonate linkage.

The term "modified oligonucleotide" also encompasses oligonucleotides with a modified base and/or sugar. For example, a 3', 5'-substituted oligonucleotide is a modified oligonucleotide having a sugar which, at both its 3' and 5' positions is attached to a chemical group other than a hydroxyl group (at its 3' position) and other than a phosphate group (at its 5' position). A modified oligonucleotide may also contain at least one 2'-substituted ribonucleotide. In one embodiment, the ribose of a ribonucleotide in the modified oligonucleotide is a 2'-O-allyl, 2'-O-alkyl (such as a 2'-O-methyl) or 2'-O-aryl, 2'-halo, or 2'-amino.

A modified oligonucleotide may also be a capped species. In addition, unoxidized or partially oxidized oligonucleotides having a substitution in one nonbridging oxygen per nucleotide in the molecule are also considered to be modified oligonucleotides. Also considered as modified oligonucleotides are oligonucleotides having nuclease resistance-conferring bulky substituents at their 3' and/or 5' end(s) and/or various other structural modifications not found in vivo without human intervention are also considered herein as modified.

In another preferred embodiment, the oligonucleotide of the composition of the invention is covalently bonded to adamantane which is noncovalently associated with the cyclodextrin. The covalent association is between the 3'-hydroxyl or the 5'hydroxyl of the oligonucleotide and the adamantane. In other embodiments where the oligonucleotide contains a ribonucleotide, the adamantane is covalently associated with the 2'-hydroxyl of the ribonucleotide.

In another aspect of the invention, a pharmaceutical formulation is provided which includes the cyclodextrin-complexed oligonucleotide composition, preferably in a physiologically acceptable carrier. Such a formulation is useful in a method of increasing the cellular uptake, and thus, of enhancing the intracellular concentration of an exogenous oligonucleotide. The formulation is also used in a method of treating a cell, for example, for viral infection, or to prevent a viral infection.

Also provided by this invention are methods of increasing the in vivo availability of an oligonucleotide by complexing it to a cyclodextrin.

In another aspect of the invention, pharmaceutical formulations are provided which contain the oligonucleotide composition described above. These formulations are used in another aspect of the invention, namely, methods of increasing the cellular uptake and intracellular concentration of an exogenous oligonucleotide. In these methods, a cell is treated with the pharmaceutical formulation.

In yet another aspect of the invention, a method of treating a cell for viral infection, or for the prevention of viral infection, is provided. In this method, a cell is contacted with a pharmaceutical formulation containing an oligonucleotide having a nucleotide sequence complementary to a portion of the nucleic acid of a virus. Thus, the invention provides a useful composition for treating inadvertently infected cell culture lines. Contamination of cell lines with mycoplasma or viruses can be eliminated by using the compositions according to the invention.

The invention also provides methods of increasing the solubility of an oligonucleotide in vivo, including the step of noncovalently complexing a cyclodextrin to an oligonucleotide. In some embodiments, the oligonucleotide is covalently complexed with adamantane, and adamantane is noncovalently complexed to the cyclodextrin.

BRIEF DESCRIPTION OF THE DRAWINGS

The foregoing and other objects of the present invention, the various features thereof, as well as the invention itself may be more fully understood from the following description, when read together with the accompanying drawings in which:

FIG. 1A is a schematic representation of 2-hydroxypropyl-β-cyclodextrin ($C_{42}H_{70}O_{35}$);

FIG. 1B is a schematic representation of γ-cyclodextrin ($C_{48}H_{80}O_{40}$);

DETAILED DESCRIPTION OF THE PREFERRED EMBODIMENTS

Figure 2A:
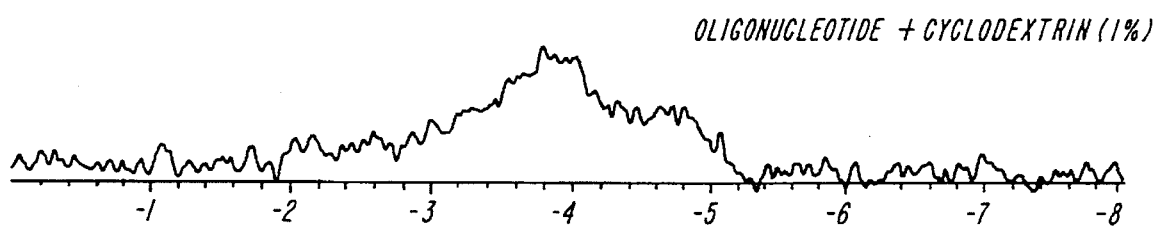
FIG. 2A is a scan of the $^{31}P$ NMR spectra of non-covalently associated oligonucleotide-cyclodextrin complex.

The patent and scientific literature referred to herein establishes the knowledge that is available to those with skill in the art. The issued U.S. patent, allowed patent applications, and articles cited herein are hereby incorporated by reference.

This invention provides oligonucleotide compositions which enhance the uptake of oligonucleotides into cells, thereby increasing the efficacy of the treatment and reducing the dose required. The compositions include an oligonucleotide complexed with a cyclodextrin or other polysaccharide.

Cyclodextrins, also known as cycloamyloses, are a group of cyclic polysaccharides consisting of six to eight naturally occurring D(+)-glucopyranose units in $\alpha$-(1,4) linkage. They are classified by the number of the glucose units they contain: alpha ($\alpha$)-cyclodextrin has six glucose units; beta ($\beta$)-cyclodextrin has seven, and gamma ($\gamma$)-cyclodextrin has eight (Brewster et al. (1989) *J. Parenteral Sci. Technol.* 43:231–240). FIGS. 1A–1B show representative cyclodextrins of these classes. Cyclodextrins as a group are cone-shaped molecules having a slightly apolar internal cavity which can accommodate the inclusion of various other molecules. Their peripheral structure contains a large number of hydroxyl groups which provide water solubility.

Some cyclodextrins and various substituted derivatives thereof, such as hydroxypropyl-, hydroxyethyl-, methyl-, or sulfate-substituted cyclodextrins, have the ability to enhance the solubility and availability of a variety of pharmacological agents. For example, 2-hydroxypropyl $\beta$-cyclodextrin (HPCD) substantially enhances solubility and uptake of some sparingly soluble drugs such as hydrophobic protein containing drugs (Brewster et al. (1991) *Pharmaceut. Res.* 8:792–795; Yaksh et al. (1991) *Life Sci.* 48:623–633) such as insulin (Merkus et al. (1991) *Pharmaceut. Res.* 8:588–592), bovine growth hormone (Simpkins et al. (1991) *J. Parenteral Sci. Technol.* 45:266–269), and methyltestosterone (Muller et al. (1991) *J. Pharmaceut. Sci.* 80:599–604). In addition, ethylated-$\beta$-cyclodextrin has been used as slow-release type carriers for hydrophilic drugs such as diltiazem (Horiuchi et al. (199) *J. Pharmaceut. Sci.* 79: 128–132).

Other cyclodextrins have unique biological features. For example, cyclodextrin sulfates have anti-inflammatory, anti-lipemic, and antiviral activity, and have been found to inhibit replication of HIV by either prevention of viral absorption or budding (Pitha et al. (1991) *J. Pharmaceutic. Res.* 8: 1151–1154; Anand et al. (199) *Antiviral Chem. Chemother.* 1:41–46); Moriya et al. (1991) *J. Med. Chem.* 34:2301–2304; Weiner et al. (1992) *Pathobiol.* 60:206–212). In addition, cyclodextrin sulfates have protective effects on gentamicin-induced nephrotoxicity (Uekama et al. (1993) *J. Pharm. Pharmacol.* 45:745–747) and on hemolysis of erythrocytes (Weisz et al. (1993) *Biochem. Pharmacol.* 45: 1011–1016).

Since cyclodextrins are biocompatible polymers composed of naturally occurring D-glucose subunits, their therapeutic application has been regarded as relatively safe. Indeed, in vivo administration of cyclodextrin concentrations of 5 to 10% has been generally used to enhance adsorption of drugs in animal studies, and no significant cytotoxic effects have been reported. (Gerloczy et al. (1994) *Pharmaceut. Sci.* 83:193–196).

Besides standard intravenous administration, cyclodextrins can be easily absorbed through nasal (Merkus et al. (1991) *Pharm. Res.* 8: 588–592; Shao et al. (1992) *Pharm. Res.* 9: 1157–1163), intestinal (Nakanishi et al. (1992) *Chem. Pharm. Bull.* 40: 1252–1256), corneal (Jansen et al. (1990) *Lens Eye Tox. Res.* 7:459–468), rectal epithelium (Arima et al. (1992) *J. Pharm. Soc. Japan* 112:65–72), and by transdermal injection (Yoshida et al. (1990) *Chem. Pharm. Bull.* 38: 176–179).

In addition, cyclodextrins have also been found to eliminate some of the undesirable side-effects of the drugs to which they have been complexed. For example, when used as a vehicle in ophthalmic eye-drop formulations, 2-hydroxypropyl-$\beta$-cyclodextrin can suppress the immune reaction to a corneal graft (Arima et al. (1992) *J. Pharmaceut. Soc. Japan* 112:65–72) and is not toxic to the corneal epithelium.

Cyclodextrins can be prepared by methods known in the art (see. e.g., Moriya et al. (1993) *J. Med. Chem.* 36:1674–1677) and are commercially available.

The oligonucleotides to which the cyclodextrin is complexed are composed of deoxyribonucleotides, ribonucleotides, or a combination of both, with the 5' end of one nucleotide and the 3' end of another nucleotide being covalently linked. These oligonucleotides are at least 6 nucleotides in length, but are preferably 10 to 50 nucleotides long, with 15 to 30mers being the most common. Oligonucleotides can be prepared by art recognized methods such as phosphoramidate or H-phosphonate chemistry which can be carried out manually or by an automated synthesizer as described by Brown in *A Brief History of Oligonucleotide Synthesis. Protocols for Oligonucleotides and Analogs, Methods in Molecular Biology* (1994) 20:1–8).

The oligonucleotides of the composition may also be modified in a number of ways without compromising their ability to hybridize to the target nucleic acid and to complex with adamantane and/or cyclodextrin. For example, the oligonucleotides may contains other than phosphodiester internucleotide linkages between the 5' end of one nucleotide and the 3' end of another nucleotide in which the 5' nucleotide phosphate has been replaced with any number of chemical groups. Examples of such chemical groups include alkylphosphonates, phosphorothioates, phosphorodithioates, alkylphosphonothioates, alkylphosphonates, phosphoramidates, phosphate esters, carbamates, acetamidate, carboxymethyl esters, carbonates, and phosphate triesters. Oligonucleotides with these linkages can be prepared according to known methods (see, e.g., Sonveaux "Protecting Groups in Oligonucleotides Synthesis" in Agrawal (1994) *Methods in Molecular Biology* 26:1–72; Uhlmann et al. (1990) *Chem. Rev.* 90:543–583).

Other modifications include those which are internal or at the end(s) of the oligonucleotide molecule and include additions to the molecule of the internucleoside phosphate linkages, such as cholesteryl or diamine compounds with varying numbers of carbon residues between the amino groups and terminal ribose, deoxyribose and phosphate modifications which cleave, or crosslink to the opposite chains or to associated enzymes or other proteins which bind to the viral genome. Examples of such modified oligonucleotides include oligonucleotides with a modified base and/or sugar such as arabinose instead of ribose, or a 3', 5'-substituted oligonucleotide having a sugar which, at both its 3' and 5' positions is attached to a chemical group other than a hydroxyl group (at its 3' position) and other than a phosphate group (at its 5' position). Other modified oligonucleotides contain at least one 2'-substituted ribonucleotide in which the 2'-OH of the ribose molecule is substituted with an -O-lower alkyl containing 1–6 carbon atoms, aryl or substituted aryl or allyl having 2–6 carbon atoms, e.g., 2'-O-allyl, 2'-O-aryl, 2'-O-alkyl (such as a 2'-O-methyl), 2'-halo, or 2'-amino, but not with 2'-H, wherein allyl, aryl, or alkyl groups may be unsubstituted or substituted, e.g., with halo, hydroxy, trifluoromethyl, cyano, nitro, acyl, acyloxy, alkoxy, carboxyl, carbalkoxyl or amino groups.

Yet other modified oligonucleotides are capped with a nuclease resistance-conferring bulky substituent at their 3' and/or 5' end(s), or have a substitution in one nonbridging oxygen per nucleotide. Such modifications can be at some or all of the internucleoside linkages, as well as at either or both ends of the oligonucleotide and/or in the interior of the molecule.

Oligonucleotides which are self-stabilized are also considered to be modified oligonucleotides useful in the methods of the invention (Tang et al. (1993) Nucleic Acids Res. 20:2729–2735). These oligonucleotides comprise two regions: a target hybridizing region; and a self-complementary region having an oligonucleotide sequence complementary to a nucleic acid sequence that is within the self-stabilized oligonucleotide.

The oligonucleotides complexed to the cyclodextrin can have any nucleotide sequence desired and are able to hybridize to RNA or DNA under normal physiological conditions existing within a cell harboring the target nucleic acid. Such conditions include pH, temperature, and ionic conditions characteristic of the mammalian cellular environment.

The preparation of these unmodified and modified oligonucleotides is well known in the art (reviewed in Agrawal et al. (1992) Trends Biotechnol. 10: 152–158). For example, nucleotides can be covalently linked using art-recognized techniques such as phosphoramidate, H-phosphonate chemistry, or methylphosphoramidate chemistry (see, e.g., Uhlmann et al. (1990) Chem. Rev. 90: 543–584; Agrawal et al. (1987) Tetrahedron. Lett. 28: (31): 3539–3542); Caruthers et al. (1987) Meth. Enzymol. 154:287–313; U.S. Pat. No. 5,149,798). Oligomeric phosphorothioate analogs can be prepared using methods well known in the field such as methoxyphosphoramidite (see, e.g., Agrawal (1988) Proc. Natl. Acad. Sci. (USA) 85:7079–7073) or H-phosphonate chemistry (see, e.g., Froehler, "Oligonucleotide Synthesis: H-phosphonate Approach" in Agrawal (1994) Meth. Mol. Biol. 20:63–80).

An oligonucleotide can be noncovalently complexed to a cyclodextrin by mixing them together in an aqueous solution such as a cellular growth medium or various buffers.

Alternatively, an oligonucleotide can be covalently linked to an adamantane molecule which is then noncovalently linked to the cyclodextrin. Adamantane enters into the cavity of a cyclodextrin and forms a stable, noncovalent complex with it (Brinker et al. (1993) Angew. Chem., Int. Ed. Engl. 32: 1344–1345, Ueno et al. (1993) J. Am. Chem. Soc. 115:12575–12576).

Linkage of the adamantane molecule can be accomplished at the 3'-hydroxyl or 5'-hydroxyl terminus of the oligonucleotide having a (or both) deoxyribonucleotide terminal residue(s) termini. Alternatively, adamantane can be covalently complexed with the 2'-hydroxyl of a ribonucleotide residue. This can be accomplished with a linker phosphoramidite or H-phosphonate as the final coupling step in machine-aided assembly of an oligonucleotide, as has been used for the attachment of single reporter groups to a synthetic oligonucleotide (see, e.g., Agrawal et al. (1986) Nucleic Acids Res. 14:6229–6245; Misiura et al. (1990) Nucleic Acids Res. 18:4345–4354; Nelson et al. (1992) Nucleic Acids Res. 20:6253–6259).

Covalent linkage of adamantane to the oligonucleotide can also be accomplished with the aid of an amino linker as described by Misiura et al. (J. Nucleic Acids Res. (1990) 18:4345–4353). The adamantane-linked oligonucleotide is then noncovalently associated with the cyclodextrin by mixing the two in an aqueous medium or buffer (see, e.g., Simpkins et al. (1991) J. Parental Sci. & Technol. 45:266).

The oligonucleotide composition or therapeutic formulation including the composition is useful in methods of increasing the cellular uptake and enhancing the intracellular concentration of an exogenous oligonucleotide, in methods of increasing the solubility of an oligonucleotide in vivo, and in methods of treating a cell, for example, for viral infection, or to prevent a viral infection.

Figure 2B:
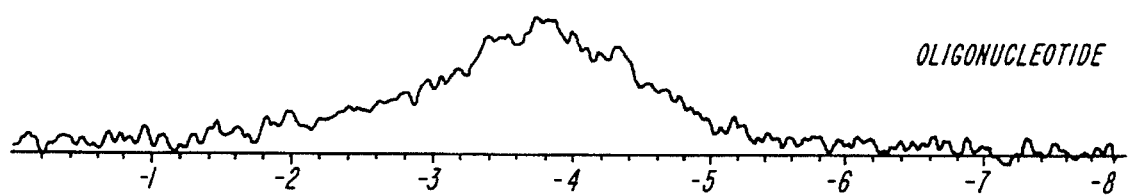
FIG. 2B is a scan of the $^{31}P$ NMR spectra of oligonucleotide.
Figure 3:
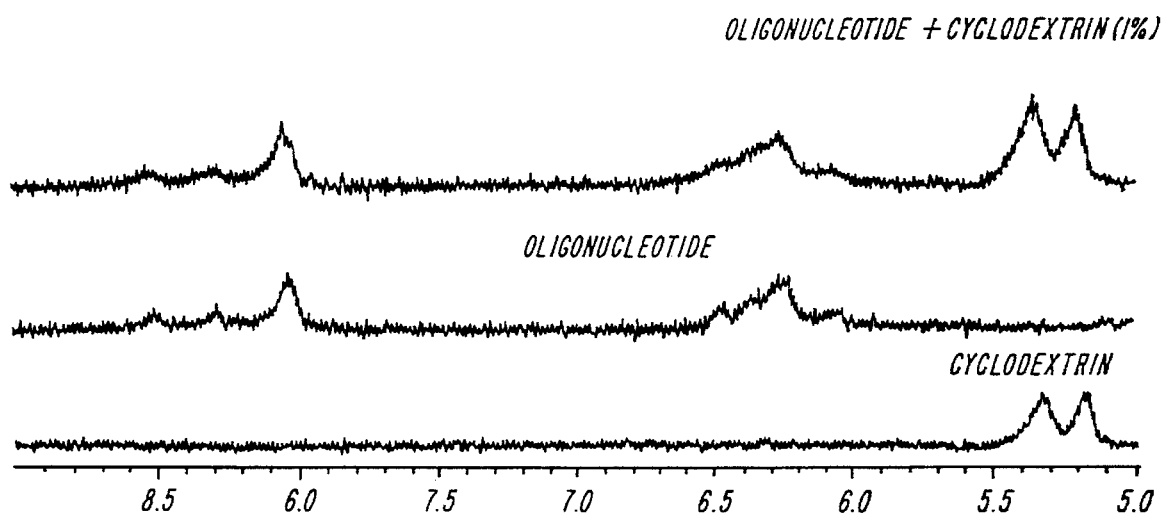
FIG. 3 is a scan of the $^{1}H$ NMR spectra of non-covalently associated oligonucleotide-cyclodextrin complex, oligonucleotide and cyclodextrin.

That the cyclodextrin is able to complex noncovalently with the oligonucleotide was confirmed by NMR spectrometry. The phosphorous spectrum of the complexed oligonucleotide in an oligonucleotide-cyclodextrin mixture shown in FIG. 2A has a split pattern. Before mixing the phosphorus spectrum of the oligonucleotide was only a broad peak (FIG. 2B), an indication of a short distance interaction between the oligonucleotide and the cyclodextrin. The $^1$H NMR spectra in FIG. 3 demonstrates that upon the mixing of the oligonucleotide and the cyclodextrin, the signals of the sugar proton H1 of the oligonucleotide broadened (arrow), indicative of a phenomenon of local environment change around H1's, due to the interaction of cyclodextrin with the sugar of the nucleotides. Therefore, cyclodextrin is able to complex noncovalently with an oligonucleotide.

That cyclodextrin-complexed oligonucleotides are taken up by cells was confirmed as follows. Fluorescein (FITC)-conjugated phosphorothioate (PS) oligonucleotides were complexed with cyclodextrin either at 4° C., overnight or at 25° C. for 1 hour. A cultured T cell leukemia cell line (CEM) was then contacted with the treated oligonucleotides. The fluorescent intensity of the CEM cells was measured by computer-analyzed flow cytometry.

Figure 4:
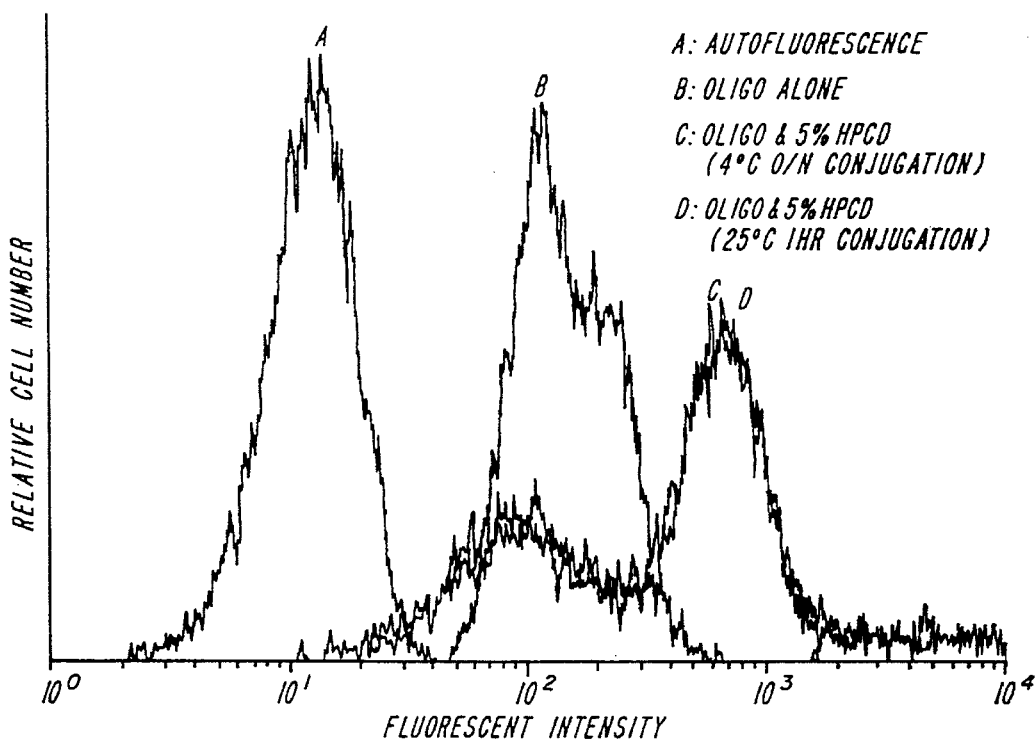
FIG. 4 is a flow cytometry data output record showing the fluorescent intensity of cell cultures treated with (A) no oligonucleotides; (B) PS oligonucleotide; (C) cyclodextrin-complexed PS oligonucleotide at 4° C. over night; or (D) cyclodextrin-complexed PS oligonucleotide at 25° C. for 1 hour.

As shown in the computer-generated scans in FIG. 4, the fluorescent intensity is greatly increased when the oligonucleotide is complexed with cyclodextrin, indicating that complexation greatly increases cellular uptake.

Figure 5A:
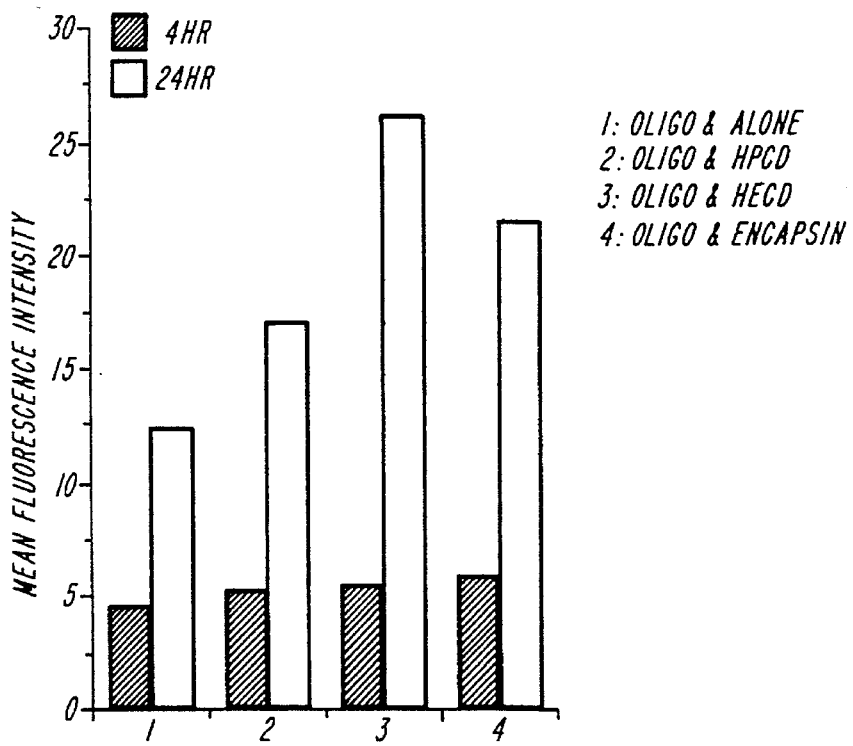
FIG. 5A is a bar graph comparing the fluorescence of cells treated with FITC-labelled oligonucleotide-cyclodextrin complexes 4 hours and 24 hours after administration.
Figure 5B:
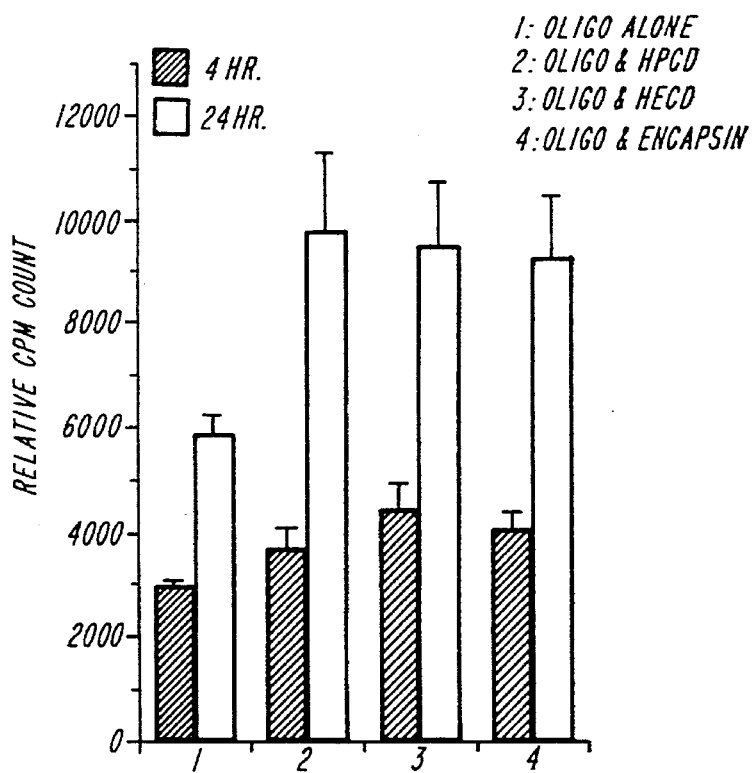
FIG. 5B is a bar graph comparing the radioactivity of $^{35}S$-labelled oligonucleotide-cyclodextrin complexes 4 hours and 24 hours after administration.
Figures 6A, 6B, 6C, 6D:
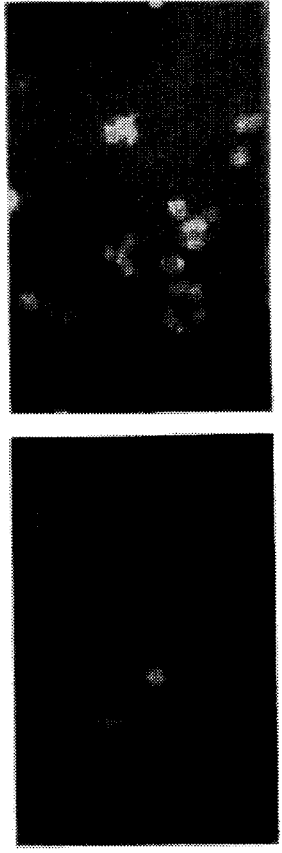
FIG. 6A is a photograph of a fluorescent micrograph showing cells treated with FITC-linked 20mer PS-oligonucleotide.
FIG. 6B is a photograph of a fluorescent micrograph showing cells with FITC-linked 20mer complexed with cyclodextrin.
FIG. 6C is a photograph of a fluorescent micrograph showing cells treated with FITC-linked 42mer PS-oligonucleotide.
FIG. 6D is a photograph of a fluorescent micrograph showing cells with FITC-linked 42mer complexed with cyclodextrin.

Additional experiments with other human cell types and various types of cyclodextrins complexed to oligonucleotides further demonstrate this point. Cells from a cultured human T cell leukemic cell line (H9) were incubated with fluorescent-labelled oligonucleotide-cyclodextrin complexes. At 4 and 24 hours, the fluorescent intensity of the H9 cells was measured by computer-analyzed flow cytometry. Data was gated on living cells. The results shown in FIG. 5A demonstrate that fluorescent intensity in these cells, and hence, uptake of oligonucleotides, is greatly enhanced in the presence of cyclodextrins. To provide additional evidence that the difference in cyclodextrin mediated oligonucleotide uptake observed was not an artifact of the fluorescent-labelled oligonucleotide, some of experiments were repeated and confirmed with $^{35}$S-labelled phosphorothioate oligodeoxynucleotides. In these tests cells were incubated with $^{35}$S-labelled oligonucleotide-cyclodextrin complexes. At 4 and 24 hours, radioactivity in the cells was measured by removing an aliquot of cell culture, washing it, spotting it onto a filter paper, and counting it. The results of one representative experiment are shown in FIG. 5B. Because these results are similar to those obtained in the fluorescent labelling experiments, uptake is not an artifactual result of the fluorescent labelling.

To determine whether the size of oligonucleotide affects the ability of the cyclodextrin to affect cellular uptake, 20mer and 42mer FITC-conjugated PS-oligonucleotides were contacted with cyclodextrin at 25° C. for 1 hour and then were added to CEM cells. The cells were examined under a fluorescent microscope.

As shown in the fluorescence micrographs in FIGS. 6A–6D, both the 20mer and the 42mer oligonucleotides which were complexed with cyclodextrin were taken up by the cells. Furthermore, more fluorescent cells were detected after treatment with oligonucleotides complexed with cyclodextrin than after treatment with uncomplexed oligonucleotides. This indicates that oligonucleotide uptake is enhanced by complexing with cyclodextrin, independent of oligonucleotide length.

Figure 7:
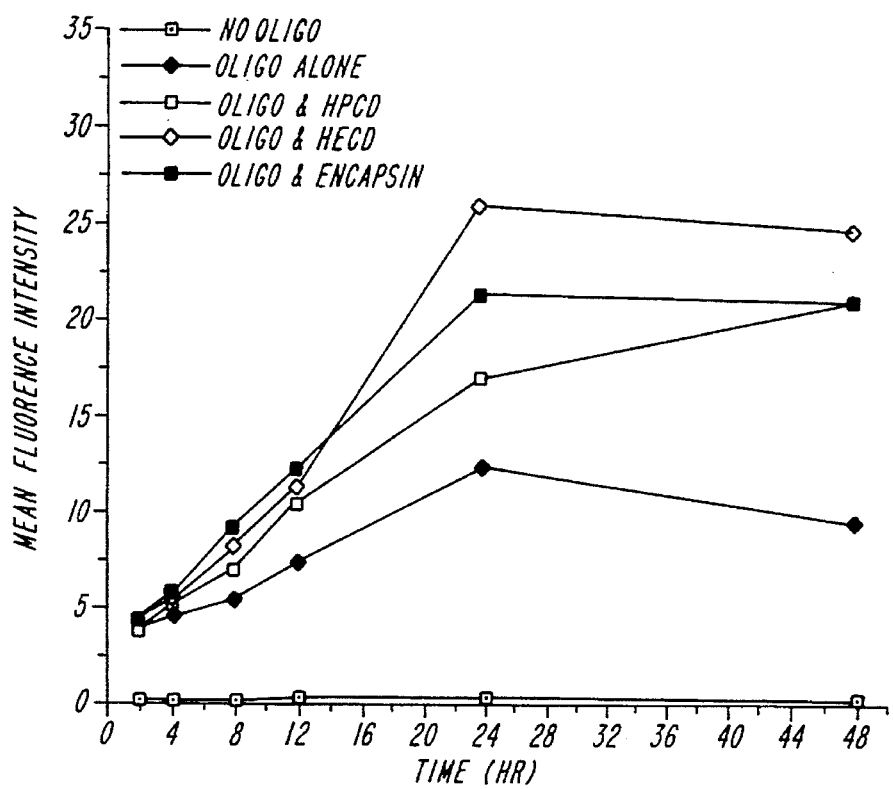
FIG. 7 is a graphic representation of the uptake of FITC-labelled oligonucleotide-cyclodextrin complexes into cell cultures over time.

To determine whether complexation of the oligonucleotides with cyclodextrin increased the time during which the oligonucleotides are taken up by the cells, cells were measured for fluorescence intensity at different time points after the administration of FITC-labelled-oligonucleotide-cyclodextrin complex. The results in FIG. 7 show that uptake of oligonucleotide complexed with HPCD increases to beyond 48 hours, in contrast to uptake of uncomplexed oligonucleotides which levels out after 24 hours.

To determine whether linkage of the cyclodextrin-associated oligonucleotide to adamantane had an effect on their uptake into cells, cells were treated for varying amounts of time with fluorescently (FITC) labelled oligonucleotide, fluorescently labelled, cyclodextrin-associated oligonucleotide, or fluorescently labelled, covalently-linked adamantane/oligonucleotide associated with cyclodextrin. The fluorescence intensity of the cells was then analyzed by flow cytometry.

Figure 8:
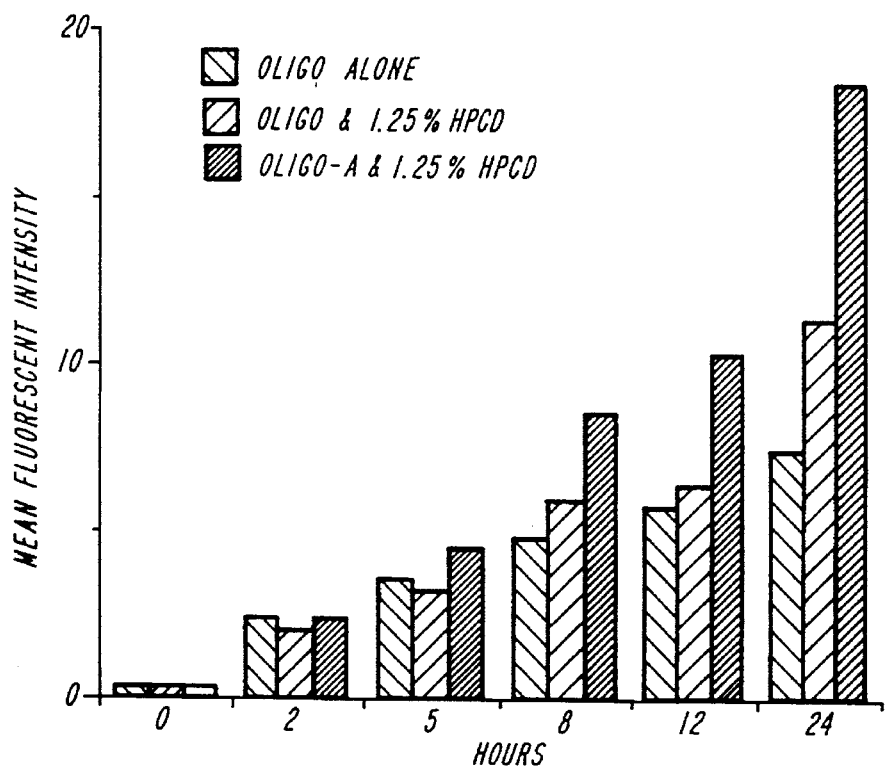
FIG. 8 is a graphic representation of the fluorescent intensity of cell cultures treated with FITC-labelled uncomplexed, cyclodextrin-complexed, and cyclodextrin-adamantane complexed PS-oligonucleotides.

As shown in FIG. 8, FITC oligonucleotide uptake into cells increased gradually during the time course studied. In the presence of cyclodextrin, the increase is much more dramatic, with the increase being the greatest with adamantane-linked oligonucleotides (oligonucleotide-A). Thus, covalent linkage of oligonucleotides to adamantane enhances the cellular uptake of cyclodextrin-associated oligonucleotides.

To administer the pharmaceutical formulation of the invention, the cycloxdextrin-associated or adamantane-linked, cyclodextrin-associated oligonucleotide is mixed with a physiologically acceptable carrier and then injected intravenously, intramuscularly, intraperitoneally, or by intranasal (Merkus et al. (1991) *Pharmaceut. Res.* 8:588–592; Shao et al. (1992) *Pharmaceut. Res.* 9:1157–1163), oral, transdermal, or subcutaneous administration. Cyclodextrins can also be easily absorbed through intestinal (Nakanishi et al. (1992) *Chem. Pharm. Bull.* 40: 1252–1256), corneal (Jansen et al. (1990) *Lens Eye Toxicity Res.* 7:459–468), and rectal (Arima et al. (1992) *J. Pharmaceut. Soc. Japan* 112:65–72) epithelium, and by transdermal injection (Yoshida et al. (1990) *Chem. Pharmaceut. Bull.* 38:176–179). Effective dosages of the oligonucleotide and modes of its administration in the treatment of the particular disorder for which the oligonucleotide is being administered can be determined by routine experimentation. The pharmaceutical forms suitable for injectable or other use include sterile aqueous solutions or dispersions and sterile powders for the extemporaneous preparation of sterile injectable solutions or dispersions. In all cases the form must be sterile. It must be stable under the conditions of manufacture and storage and may be preserved against the contaminating action of microorganisms, such as bacteria and fungi. The carrier can be a solvent or dispersion medium. The prevention of the action of microorganisms can be brought about by various antibacterial and antifungal agents. Prolonged absorption of the injectable therapeutic agents can be brought about by the use of the compositions of agents delaying absorption.

The following examples illustrate the preferred modes of making and practicing the present invention, but are not meant to limit the scope of the invention since alternative methods may be utilized to obtain similar results.

EXAMPLES

1. Preparation of Oligonucleotides

PO- and PS-oligonucleotides were synthesized on an automated synthesizer (Millipore 8700, Millipore Corp., Bedford, Mass.) using phosphoramidate chemistry (see Agrawal et al. (1989) *Proc. Natl. Acad. Sci.* (*USA*) 86:7790–7794; McBride et al. (1983) *Tetrahedron Lett.* 24:245). The oxidation reagents used in the syntheses were standard solution of iodine, for phosphodiester linkages, and 3H-1,2-benzodithiole-3-one-1,1-dioxide as a solution of 1 g in 100 ml of acetonitrile, for phosphorothioate linkages formation. Methylphosphonates were prepared according to the method of Beaucage, "Oligonucleotide Synthesis: Phosphramidite Approach" in *Protocols for Oligonucleotides and Analogs, Methods in Molecular Biology* (1994) 20:33–62). Oligonucleotide concentrations were determined by absorbance at 260 nm, taking into account the molar extinction coefficient of the nucleotides present in each sequence (Ausubel et al. (eds.) *Current Protocols in Molecular Biology* (1987) Wiley, New York).

2. FITC-Labelling of Oligonucleotides

Fluorescein (FITC) was conjugated to the oligonucleotides through the 5'-hydroxyl using a fluorescein amidite (Clontech Laboratories, Inc., Palo Alto, Calif.) according to the method of Schubert (*Nucleic Acids Res.* (1990) 18:3427). All oligonucleotides were deprotected by treatment with concentrated ammonia at 55° C. for 12 hours. The oligonucleotides were purified by polyacrylamide gel electrophoresis (PAGE), desalted by Sep-Pak C18 cartridges (Waters, Milliford, Mass.) and lyophilized to dryness prior to use.

3. Preparation of Cyclodextrins 2-hydroxypropyl-β-cyclodextrin (HPCD) was prepared according to the method of Pitha et al. (*Int. J. Pharm.* (1986) 29:73–82) or obtained commercially from, e.g., Sigma Chemical Co., St. Louis, Mo.). HPCD as well as hydroxyethyl-β-cyclodextrin (HECD) and encapsin-β-cyclodextrin, (which is a mixture of various hydroxypropyl-β-cyclodextrins) were obtained commercially (e.g., from Amaizo, Hammond, Ind.). Other cyclodextrins such as α-($C_{36}H_{60}O_{30}$) cyclodextrin and γ-($C_{48}H_{80}O_{40}$) cyclodextrin are also commercially available (e.g., from, Sigma Chemical Co., St. Louis, Mo.), and trimethyl β-cyclodextrin, hydroxypropyl cyclodextrin, and sulfated β-cyclodextrin (e.g., from Amaizo, Hammond, Ind.).

4. Preparation of FITC-Labelled, HPCD-Associated Oligonucleotide

Cyclodextrins were sterilized by being passed through a 0.2 μM polycarbonate filter (Corning, Corning, N.Y.) for cell culture studies. 1 μg of fluorescent (FITC) conjugated PS-oligonucleotides were mixed with 5–10% HPCD in 75 μl RPMI medium. The mixtures were kept either at 4° C. for overnight or at 25° C. for 1 hour for noncovalent complexation. (Simpkins et al. (1991) *J. Parental Sci. & Technol.* 45:266).

Alternatively, oligonucleotides were mixed with HPCD, HECD, or encapsin-β-cyclodextrin at a 2×concentration (final concentration of oligonucleotide being 10 μg/ml) in RPMI medium (JRH Biosciences, Lenexa, Kans.), sonicated at 4° C. for 2 hours, and incubated overnight at 4° C.

5. Radioactively Labelling of Oligonucleotides

Oligonucleotides were 5' end labelled by incubating 200 ng oligonucleotide (PO or PS) with 2 μl polynucleotide kinase (Pharmacia, Piscataway, N.J.), and 2 μl of (α-$^{32}$P)ATP (Amersham LIFE Science, Arlington Heights, Ill.) in a final volume of 20 μl at 37° C. for 1 hour. The mixture was passed over a Sephadex G-25 column (5 Prime-3 Prime, Boulder, Colo.) to separate the $^{32}$P-labelled oligonucleotide from the unlabelled oligonucleotide.

Oligonucleotides were labelled with $^{35}$S using the H-phosphonate approach of Agrawal et al. (*Proc. Natl. Acad. Sci.* (USA) (1991) 88:7595–7599. Briefly, five milligrams of oligodeoxynucleoside H-phosphonate bound to controlled-pore glass was oxidized with a mixture of $^{35}S_8$ (5 mCi, 1 Ci/mg, Amersham (LIFE Science, Arlington Heights, Ill.); 1 Ci=37 GBq) in 40 μl of carbon disulfide/pyridine/triethylamine (9:9:1). After 30 min, 100 μl of 7% (wt/vol) unlabelled $S_8$ in the same solvent mixture was added and the reaction continued for another 60 min. The solution was removed and the support was washed with carbon disulfide (3×500 μl) and with acetonitrile ammonia (55° C., 14 hr), evaporated, and desalted with a Sep-Pak $C_{18}$ column (Waters, Milford, Mass.).

6. Preparation of Radioactively Labelled Cyclodextrin-Associated Oligonucleotide Half of the $^{32}$P-labelled oligonucleotide (PO or PS), together with 7 μg of corresponding unlabelled oligonucleotide (PO or PS) were mixed with 10% HPCD in 175 μl of plain RPMI medium and set at 4° C. for overnight noncovalent conjugation. Another half of the $^{32}$P-labelled oligonucleotide was set up the same way except without HPCD in the solution (control).

$^{35}$S-labelled oligonucleotide-cyclodextrin complexes were prepared by mixing the labelled oligonucleotides with cyclodextrins at 2× concentration in plain RPMI medium (such that the final concentration of oligonucleotide is 10 g/ml), sonicating the mixture at 4° C. for 2 hours, and then incubating it at 4° C. overnight.

7. Preparation of Covalently-Associated Oligonucleotide/Adamantane Complex

A. Linker-Adamantane Complex

Figure 9:
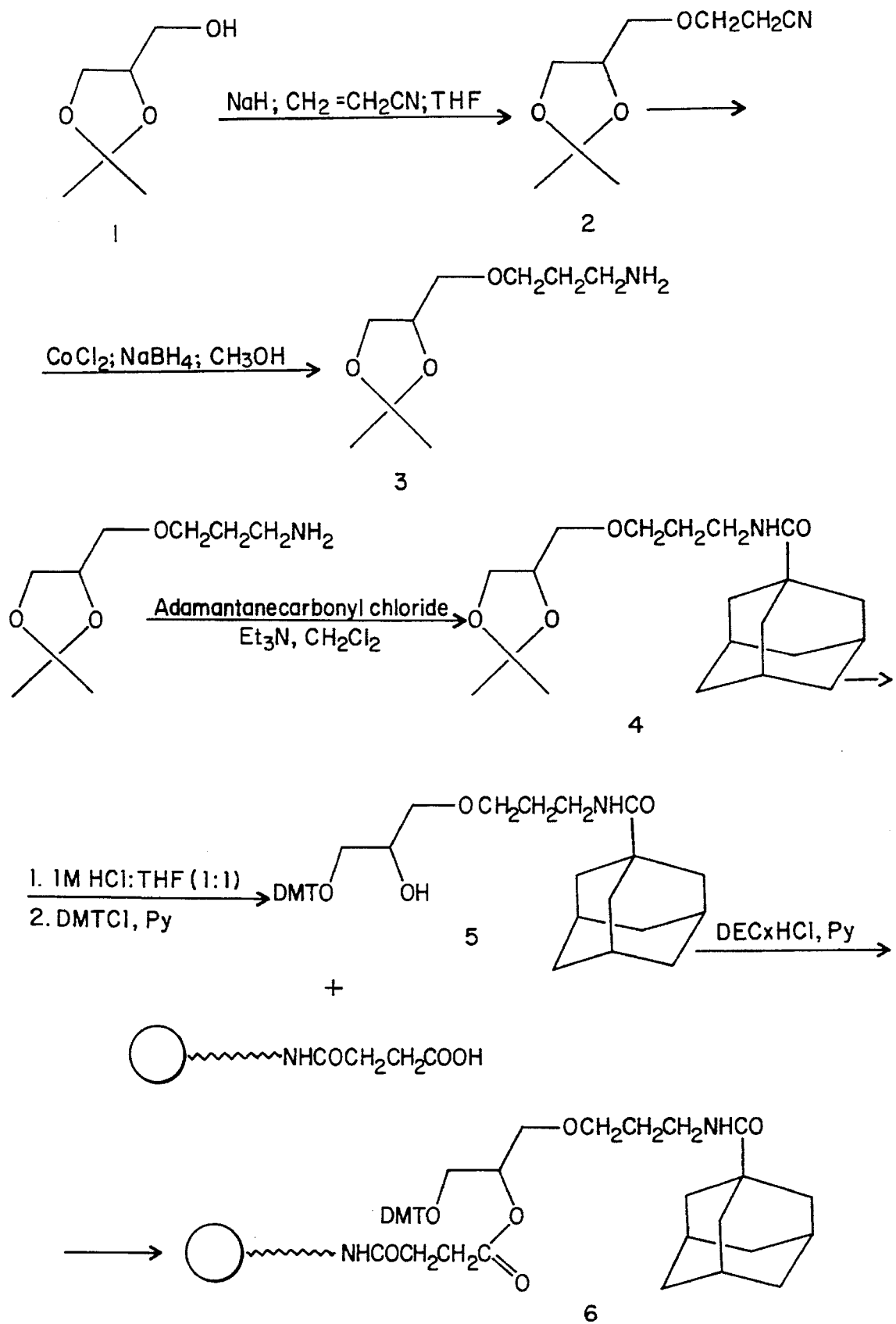
FIG. 9 is a schematic representation of the preparation of adamantane-linked CPG beads.
Figure 10:
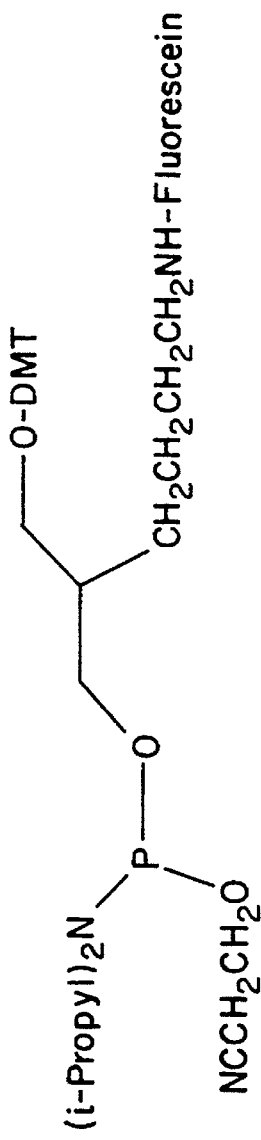
FIG. 10 is a schematic representation of fluorescein phosphoramidite used to label oligonucleotides.

Synthesis of an amino linker was performed according to the method of Misiura et al. (*J. Nucleic Acid Res.* (1990) 18:4345–4354) (FIG. 9). Briefly, reaction of readily available solketal (compound 1) with acrylonitrile in the presence of sodium hydride in tetrahydrofuran (THF) resulted in the addition product 2-cyanoethyl solketal (compound 2). Reduction of nitrile (compound 2) using sodium borohydride in the presence of cobalt (II) chloride in methanolic solution gave 3-aminopropyl solketal (compound 3) which was purified by fraction distillation.

Compound 3 was reacted with 1-adamantanecarbonyl chloride to give N-adamantoyl-3-aminopropyl solketal (compound 4). More specifically, 5.0 g (26.42 mmole) of compound 3 was dissolved in dry dichloromethane (50 ml) under inert atmosphere of $N_2$. To a solution was added dry triethylamine (4.2 ml, 3.04 g, 30.0 mmole) via syringe, following by dropwise addition of a solution of adamantanecarbonyl chloride (5.2 g, 260 mmole) in 10 ml dry dichloromethane. The solution was left to stir at room temperature for 1 hour and then concentrated. The residue was dissolved in 100 ml dichloromethane and washed with saturated sodium bicarbonate solution (3×50 ml) and the organic extracts were combined, stirred, and evaporated to dryness. The oily residue was purified on silica gel column (300 g) and eluted with a mixture of dichloromethane: methanol in ratio 19:1, to give 8.84 g (97%) compound 4.

To prepare compound 5 (1-O-(4,4'-dimethoxytrityl)-3-O-(N-adamantoyl-3-aminopropyl) glycerol), 8.56 g, (24.35 mmole) compound 4 was dissolved in a mixture of THF (48.7 ml) and 1M aqueous HCl (48.7 ml). The solution was stirred at room temperature for 30 minutes. 50 ml absolute ethanol (50 ml) was then added. The solution was concentrated, the residue was redissolved in 50 ml absolute ethanol, and the solution concentrated again. The resultant product was dried by co-evaporation with pyridine (2×50 ml) to give an oil which was redissolved in dry pyridine (150 ml). 8.25 g (24.35 mmole) 4,4'-dimethoxytrityl chloride was then added in two portions with stirring for 15 minutes. The resulting solution was left for 1 hour. 50 ml absolute ethanol was added and the solution was concentrated. The residue was dissolved in 200 ml dichloromethane and then washed with saturated sodium bicarbonate solution (2×60 ml). The aqueous layer was washed with dichloromethane (2×30 ml) and the organic extracts were combined, dried and evaporated. The residue was chromatographed on silica column (300 g) and eluted with a mixture of dichloromethane: methanol (19:1) to give a white foamy product (9.16 g (61.3%).

Compound 5 was further attached to long chain alkylamidopropanoic acid-controlled pore glass (CPG) beads, since the carboxyl moiety could be esterified with the free hydroxyl group of compound 5 in the presence of 1-(3-dimethylaminopropyl)-3-ethylcarbodiimide hydrochloride, using standard procedures (Damha et al. (1990) *Nucleic Acids Res.* 8:3813–3821) to give compound 6. Loading was 22.1 μmole/g CPG.

Approximately 10 mg of compound 6 was placed in a 10 ml volumetric flask and treated with 0.2 ml of HClO$_4$-EtOH (3:2) for 1 minute to release the dimethoxytrityl group. Then, 9.8 ml of acetonitrile was added and the absorbance of light at 498 nm was measured to determine loading efficiency according to the equation:

$A_{498} \times 10 \times 14.3)/\text{weight CPG (mg)} = \mu\text{mole/g}$

B. Linkage of Labelled Oligonucleotide to Adamantane

Figure 11A:
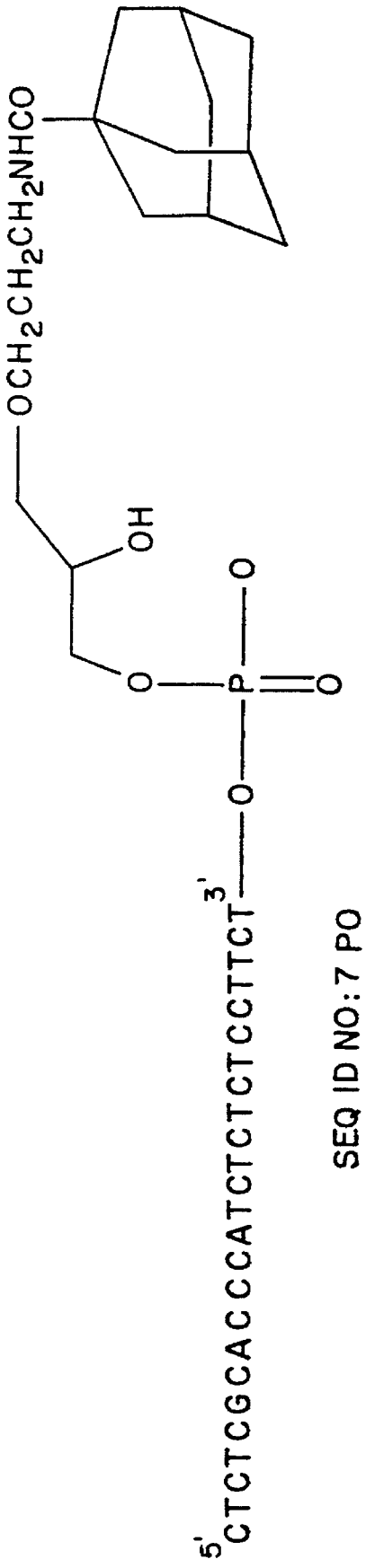
FIG. 11A is a schematic representation of a phosphodiester linked oligonucleotide covalently linked to adamantane.
Figure 11B:
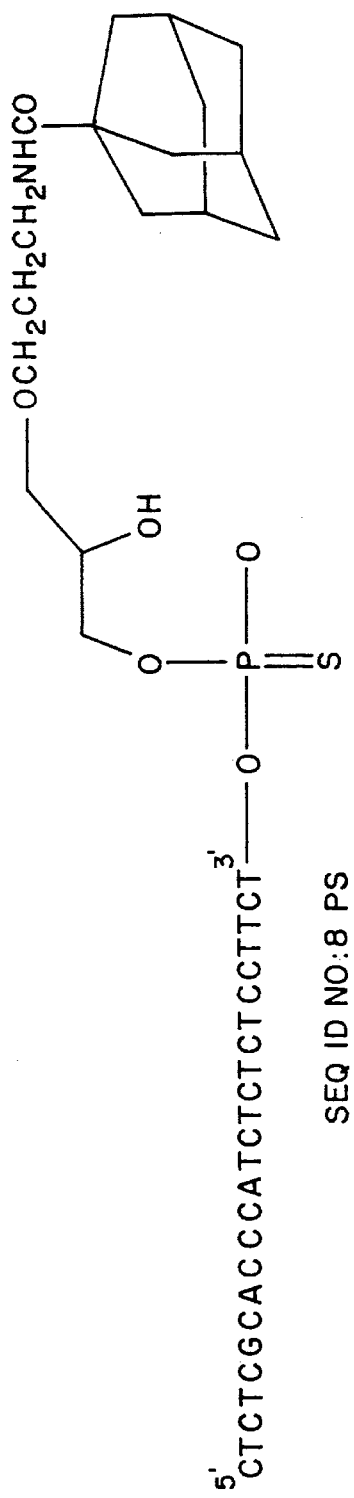
FIG. 11B is a schematic representation of a PS-oligonucleotide covalently linked to adamantane.
Figure 11C:
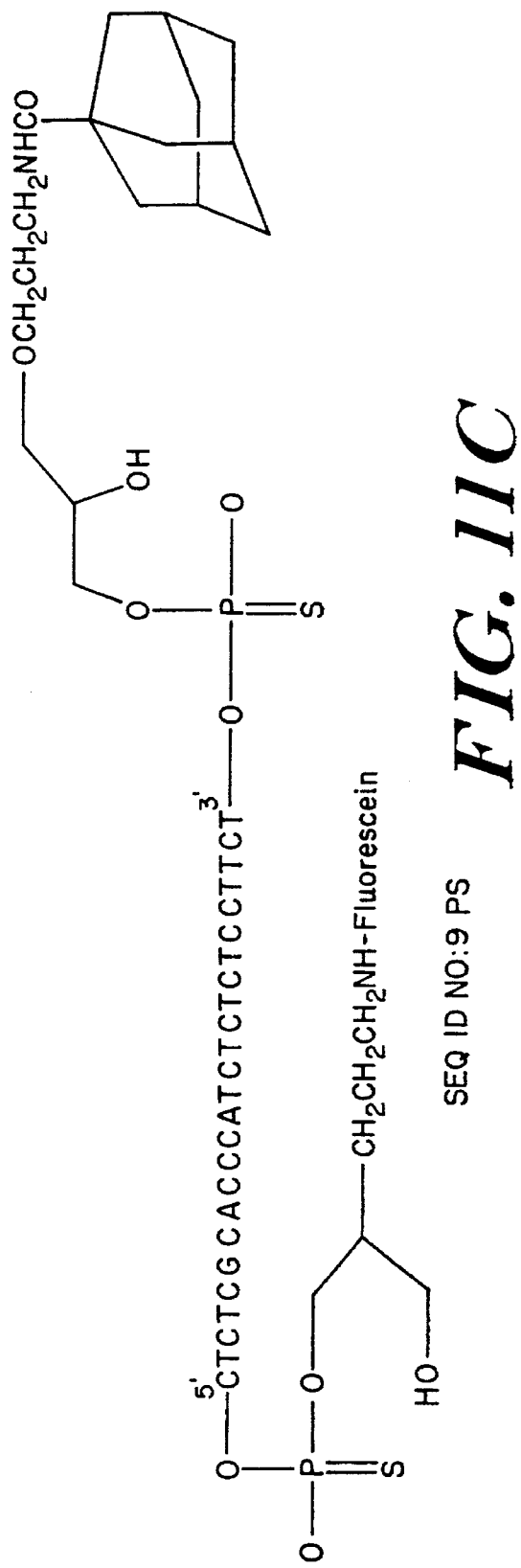
FIG. 11C is a schematic representation of a FITC-conjugated PS-oligonucleotide covalently linked to adamantane.

The phosphodiester-linked, adamantane-associated oligonucleotide (SEQ ID NO:1) (FIG. 11A), the adamantane associated PS-oligonucleotide (SEQ ID NO:1) (FIG. 11B), and the adamantane associated, FITC-conjugated PS-oligonucleotide (FIG. 11C) were cleaved off the CPG and deprotected with concentrated ammonia at room temperature for 1.5 hrs and then for 6 additional hours at 55° C. The 5'-ODMT protected oligonucleotides were purified on a preparative C-18 reverse phase column by elution with linear gradient of solvent A (0.1M ammonium acetate) and solvent B (20% 0.1M ammonium acetate+80% of acetonitrile). Detritylation was carried out by treatment with 80% aqueous acetic acid for 30 minutes at room temperature. The resulting fully deprotected oligonucleotides were purified once again on the same column by eluting with the same gradient as at DMT stage.

8. Preparation of FITC-Labelled, HPCD-Associated, Adamantane-Linked Oligonucleotide 1 μg of fluorescent (FITC) conjugated, adamantane-linked PS-oligonucleotides were mixed with 10% 2-hydroxypropyl-β-cyclodextrin (HPCD) in 75 μl plain RPMI medium. The mixtures were kept either at 4° C. for overnight or at 25° C. for 1 hour for noncovalent complexation. (Simpkins et al. (1991) *J. Parental Sci. & Technol.* 45:266).

9. Cell Culture

Human T cell leukemia cell lines CEM (Foley et al. (1965) Cancer 4:522) and Molt-3 (American Type Culture Collection, Rockville, Md., ATCC No. CRL-1552), and H9, a human T cell leukemic cell line (American Type Culture Collection, Rockville, Md., ATCC No. HTB 176) were used in these studies. Cells were cultured in RPMI medium (JRH Biosciences, Lenexa, Kans.) supplemented with 10% heat-inactivated fetal bovine serum (56° C. for 30 min.), 2 mM glutamine, 100 U/ml penicillin/streptomycin solution (JRH Biosciences, Lenexa, Kans.), $6 \times 10^{-3}$M 2-mercaptoethanol in a 5% $CO_2$–95% $O_2$ humidified air incubator at 37° C.

10. Uptake of FITC-Labelled, Cyclodextrin-Associated Oligonucleotide

CEM cells were grown to subconfluency before experiment and resuspended in RPMI medium containing 20% fetal calf serum (FCS) and the penicillin/streptomycin solution, and glutamine (as described above). 1 μg FITC oligonucleotide that had been complexed with 10% HPCD or complexed (as control) (in 75 μl of plain RPMI medium) were added to $5 \times 10^5$ CEM cells in 75 μl of RPMI medium containing 20% FCS. The final mixture contains 1 μg of FITC oligonucleotide, 5% HPCD, $5 \times 10^5$ CEM cells in 150 μl of RPMI medium Containing 10% FCS. The cells were cultured at 37° C. for 4 hours and washed with Hank's balanced salt solution (HBSS) supplemented with 0.1% BSA and 0.1% sodium azide.

The fluorescence of CEM cells were then analyzed by flow cytometry (FACScan, Beckman-Dickson, Mountain View, Calif.; or Epics XL, Coulter, Hialeah, Fla.), and analyzed with Lysis II software (when using FACScan) or Epics XL software, version 1.5 (when using Epics XL) (Zhao et al. (1993) *Antisense Res. & Dev.* 3:55). Propidium iodide (final concentration, 10 μg/ml) staining was used to distinguish viable cells from dead cells.

11. Fluorescent Microscopic Studies

20mer and 42mer fluorescent conjugated PS oligonucleotide were contacted with 5% HPCD at 25° C. for 1 hour. 1 μg oligonucleotide was added to CEM cells ($5 \times 10^5$ per tube) which were then cultured at 37° C. for 4 hours. At the end of the 4 hour culture, the cells were washed with FACS washing buffer (HBSS with 1% BSA, 1% sodium azide), and observed under a fluorescent microscope (LH50A, Olympus, Japan) (see FIGS. 6A–6D).

12. Effect of Cyclodextrin on Cellular Uptake of Adamantane-Linked Oligonucleotides Fluorescently labelled PS-oligonucleotide, or fluorescently labelled, covalently-linked adamantane/PS-oligonucleotide were mixed with 1.25% HPCD in plain RMPI medium at 4° C. for overnight complexing. 8 μg FITC-labelled oligonucleotides that had been complexed with 1.23% HPCD (as described above) or uncomplexed were added to $8 \times 10^5$ H9 cells in a final volume of 1.2 ml RMPI containing 10% fetal bovine serum. The cells were set to culture at 37° C. At various time points, aliquots of the cell culture media were taken and washed with Hank's Balanced Salt Solution (HBSS) supplemented with 1% BSA, 1% sodium azide. The fluorescence intensity of H9 cells was then analyzed by flow cytometry.

13. NMR Analysis of Oligonucleotide-Cyclodextrin Complex $^1$H NMR and $^{31}$P NMR spectra of an oligonucleotide (SEQ ID NO:2), HPCD cyclodextrin (Sigma, St. Louis, Mo.) and oligonucleotide-cyclodextrin complex in water were obtained in an NMR spectrometer (Unity 300, Varian, Palo Alto, Calif.) were dissolved in deuterium oxide (D20) (Isotec Inc., Miamisburg, Ohio) and the spectra were taken at 25° C. and 70° C.

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

---

What is claimed is:

1. A method for treating a cell infected by a virus or for the prevention of viral infection of a cell, comprising contacting the cell with an oligonucleotide covalently linked to adamantane and noncovalently complexed with a cyclodextrin, the oligonucleotide having a nucleotide sequence complementary to a portion of the nucleic acid of the virus, whereby the function of the virus is inhibited.

2. A method of reducing the dose of an antisense oligonucleotide required to effect a biological response, comprising the steps of
    (a) covalently linking the oligonucleotide to adamantane, and
    (b) non-covalently complexing the adamantane-linked oligonucleotide with a cyclodextrin,
prior to administration of the oligonucleotide.

\* \* \* \* \*